United States Patent [19]

Durette et al.

[11] Patent Number: 4,970,199

[45] Date of Patent: Nov. 13, 1990

[54] STEROIDAL GLYCOLIPIDS AS HOST RESISTANCE STIMULATORS AGAINST VIRAL INFECTION

[75] Inventors: Philippe L. Durette, New Providence; William K. Hagmann, Westfield; Mitree M. Ponpipom, Branchburg, all of N.J.

[73] Assignee: Merck & Co., Inc., Rahway, N.J.

[21] Appl. No.: 378,424

[22] Filed: Jul. 10, 1989

Related U.S. Application Data

[63] Continuation of Ser. No. 63,000, Jun. 18, 1987, abandoned.

[51] Int. Cl.$^5$ .................... A61K 31/70; A61K 31/29; A61K 31/66; A61K 31/705
[52] U.S. Cl. ........................................ 514/26; 514/43; 514/49; 514/50; 514/120; 514/134; 514/141; 514/468; 514/503; 514/885; 536/5; 536/6.2
[58] Field of Search ...................... 514/26, 885, 49, 50, 514/43, 120, 134, 141, 468, 503; 536/5, 6.2

[56] References Cited

U.S. PATENT DOCUMENTS

| | | | |
|---|---|---|---|
| 4,189,471 | 2/1980 | Ponpipom et al. | 536/5 |
| 4,228,274 | 10/1980 | Ponpipom et al. | 536/4 |
| 4,229,441 | 10/1980 | Bugianesi et al. | 536/5 |
| 4,259,324 | 3/1981 | Ponpipom et al. | 536/4.1 |
| 4,301,152 | 11/1981 | Ponpipom | 514/26 |
| 4,652,553 | 3/1987 | Hagmann et al. | 514/26 |
| 4,652,637 | 3/1987 | Hagmann et al. | 536/5 |

FOREIGN PATENT DOCUMENTS

| | | | |
|---|---|---|---|
| 0012083 | 6/1980 | European Pat. Off. | 514/26 |

OTHER PUBLICATIONS

Chabala et al; Carbohydrate Research, vol. 67: 55-63 (1978).
Ponpipom et al; Canadian Journal of Chemistry, vol. 58, 214-220 (1980).
Ponpipom et al; Journal of Medicinal Chemistry, vol. 23, No. 11, pp. 1184-1188 (1980).
Dagani; Chemical and Engineering News, Dec. 8, 1986, pp. 7-14.
Chem. Abstracts, vol. 99, 1983, 122792z, Ponpipom et al.
Chem. Abstracts, vol. 90, 1979, 23588v, Chabala et al.
Chem. Abstracts, vol. 94, 1981, 180690x, Merck.
Chem. Pharm. Bull. Jap., vol. 12, 528-532, 1964.
P.N.A.S., vol. 78, pp. 7294-7298, 1981.
J. Med. Chem., vol. 15, No. 12, pp. 1284-1287, 1972.
J. Org. Chem., vol. 43, No. 14, pp. 2923-2925, 1978, Computer Literature Search.
Surgery, vol. 92, No. 2, pp. 138-145, "Pros. for the Control of Host Defenses".
Infection, vol. 12, No. 3, pp. 230/182 to 234/86, 1984.

*Primary Examiner*—Ronald W. Griffin
*Assistant Examiner*—Nancy S. Carson
*Attorney, Agent, or Firm*—John W. Harbour; Robert J. North; Hesna J. Pfeiffer

[57] ABSTRACT

Disclosed are steroidal derivatives of glycolipids, in which steroids are bridged, via a medium length hydrocarbon chain, to 1-thio-D-mannopyranoses or 1-thio-L-fucopyranoses in combination with an anti-AIDS drug, that protect an immunocomprimised hot, particularly resulting from an AIDS-related virus, against opportunistic infection.

10 Claims, No Drawings

STEROIDAL GLYCOLIPIDS AS HOST RESISTANCE STIMULATORS AGAINST VIRAL INFECTION

This is a continuation of application Ser. No. 063,000, filed Jun. 18, 1987, now abandoned.

BACKGROUND OF THE INVENTION

1. Field of the Invention

This invention relates to steroidal derivatives of glycolipids, in which steroids are bridged, via a medium length hydrocarbon chain, to 1-thio-D-mannopyranoses or 1-thio-L-fucopyranoses that protect an immunocompromised host, particularly resulting from an AIDS-related virus, against opportunistic infection.

2. Brief Description of Disclosures in the Art

The search for new immunostimulator agents for augmenting host defenses to combat infection, cancer and congenital immunodeficiency disorders is an increasingly important area of pharmaceutical endeavor particularly as it relates to AIDS-related viruses.

Seven years ago few had ever heard of acquired immune deficiency syndrome, or AIDS. This puzzling affliction then seen in only a small number of young, homosexual men, was something new and unnamed. Today, its hard to find anyone in the U.S. who hasn't heard of AIDS, the disease that can debilitate and then kill its victim with horrific swiftness.

AIDS has come to be recognized as a public health emergency. More than 27,700 American men, women, and children have been stricken by it; the death toll is 16,000 and rising. The U.S. Public Health Service predicts that by the end of 1991 more than 179,000 persons will have succumbed to the disease.

Thus far, there is no cure for AIDS.

Technically, acquired immune deficiency syndrome (AIDS) is a transmissible deficiency of cellular immunity characterized by opportunistic infections and certain rare malignancies. The dominant risk groups for AIDS include homosexually active males, intravenous drug abusers, recipients of transfusions and blood products, and the heterosexual partners and children of high-risk individuals, suggesting the involvement of an infectious agent transmitted through intimate contact or blood products.

Recent evidence indicates that the infectious agent responsible for disease transmission is a novel lymphotropic retrovirus, currently designated HIV-I (human immunodeficiency virus) and also known as lymphadenopathy-associated virus (LAV) (Barré-Sinoussi et al., *Science* 220 868 (1983)). Similar viruses have been reported by other scientific groups (Popovic et al., *Science* 224: 497 (1984); Levy et al. *Science* 225: 840 (1984)) and designated human T-cell lymphotropic virus type III (HTLV-III), AIDS-associated retrovirus (ARV), or immune deficiency-associated virus (IDAV). Still more recent data indicates that LAV, HTLV-III, ARV and IDAV share several important characteristics, including substantial nucleotide homology (Wain-Hobson et al., *Cell* 40: 9 (1985); Muesing et al., *Nature* 313 450 (1985); Sanchez-Pescador et al., *Science* 227: 484 (1985)), and should be considered isolates of the same virus, although there is a likelihood that strain-to-strain variations among the viral isolates will exist. In addition to exhibiting substantial nucleotide homology, the isolates are similar with respect to morphology, cytopathology, requirements for optimum reverse transcriptase activity, and at least some antigenic properties (Levy, supra: Schupbach et al., *Science* 224: 503 (1984)). The above materials are hereby incorporated by reference to characterize the phrase "AIDS-related virus".

Glycolipids are known in the immunological and pharmaceutical arts, e.g. M. M. Ponpipom et al., in "Liposomes Technology Vol. III, Targeted Drug Delivery and Biological Interactions", ed. by G. Gregoriadis, CRC Critical Reviews, Ch. 7, pp. 95-115.

Steroidal glycosidic compounds are known in the art as being useful immunological adjuvants. For example see, U.S. Pat. Nos. 4,259,324; 4,229,441; 4,189,471 (all three patents being assigned to Merck & Co., Inc.); *Carbohydrate Res.* 67, pp. 55-63 (1978) by J. C. Chabala and T. Y. Shen; *J. Med. Chem.* 23, p. 1184-1188 (1980) by M. M. Ponpipom et al.; and *Can J Chem.* 58, pp. 214-220 (1980) by M. M. Ponpipom et al.

Glycosides are also known in the art for exhibiting pharmacological effects. For example, see U.S. Pat. No. 4,228,274; *Chem. Pharm. Bull. Jap.*, 12, 528-532 (1964); and *Proc. Nat'l Acad. Sci. U.S.A.*, Vol. 78, No. 12, pp. 7294-7298 (1981).

Another reference, *J. Med. Chem.*, 15, pp. 1284-1287 (1972), describes synthesis of epimeric 20and 22-azacholesterols as potential therapeutic mediators for hyperfunctioning adrenal glands.

However, the above disclosures do not specifically describe glycolipids bearing steroidal substituents for use as host resistance enhancing agents, i.e., immunostimulators specifically to viral infection in immunocompromised hosts.

SUMMARY OF THE INVENTION

By this invention there is provided a method for enhancing host resistance to viral infection in an immunocompromised individual comprising the step of administering to said individual a pharmaceutical composition consisting essentially of a compound of the formula:

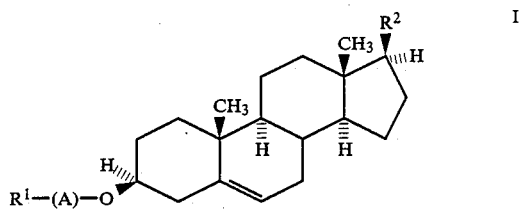

where:

$R_1$ is $\alpha$ or $\beta$-D-1-thiomannopyranose, $\alpha$ or $\beta$-L-1-thiofucopyranose;

A is $(CH_2)_n$ where n is 5-7, or $(CH_2)_k X(CH_2)_m$ where X is O, S, NH and k, m are independently 2-4 and k+m is 4-6;

$R^2$ is $C_1$-$C_8$ linear or branched alkyl or $C_2$-$C_b$ 10 linear or branched alkene;

where B is $C_1$-$C_8$ alkyl, $C_1$-$C_8$ alkoxy, $NR^3R^4$ where $R^3$ and $R^4$ are independently H, $C_1$-$C_{10}$ alkyl; $CH(CH_3)D$ where D is OH, $NH_2$, $NHR^5$ where $R^5$ is $C_1$-$C_{10}$ alkyl;

and pharmaceutically acceptable salts thereof, in an amount effective to impart resistance to viral infection, and particularly herpes simplex virus, said composition also containing a pharmaceutically acceptable carrier therefor.

Further provided is a pharmaceutical composition for enhancing nonspecific host resistance in an individual immunocompromised by an AIDS-related virus, comprising an anti-AIDS drug and a compound consisting essentially of the above-described formula: and pharmaceutically acceptable salts thereof; said composition also containing a pharmaceutically acceptable carrier thereof.

Specifically provided is where the composition contains an anti-AIDS drug selected from one or more of the following: azidothmidine, AL 721, ampligen, ansamycin, azimexon, cyclosporine, foscarnet, HPA-23, imreg-1, inosine pranobex, alpha-interferon, interleukin-2, D-penicillamine, ribavirin, suramin, CS-85, 2', 3'-dideoxycytidine, 2', 3'-dideoxyadenosine, gamma interferon, RNA deriv, Immune globulin IG-IV, thymopentin, thymostimulin, methionine-enkephalin or equivalents thereof.

Also provided is a method for enhancing resistance in a human host immunocompromised by an AIDS-related virus comprising administering to said host a pharmaceutical composition, as described above, in which method, the anti-AIDS drug can be administered in combination, concurrently or separately, with the indicated compound.

DETAILED DESCRIPTION OF THE INVENTION AND PREFERRED EMBODIMENTS

The glycolipid compositions described herein provide very high levels of protection against opportunistic infections in immunocompromised animals and humans.

By the term "AIDS-related virus" is meant the commonly designated HIV series (human immunodeficiency virus) formerly called HTLV and LAV, and species thereof, as described above in the indicated incorporated references.

These compositions may be used prophylactically to protect immunosuppressed animals or patients against infection by opportunistic organisms. In human medicine, the market includes surgery patients, burn victims, cancer patients receiving chemotherapy, aplastic anemics, diabetics, and military recruits. In animal health, the primary potential use markets include major segments of the worldwide economic animal populations during stressful shipping, mixing, and early life adaptation periods.

By the term "adjuvant" as used herein is meant a material which can be employed to potentiate the antibody response of specific antigenic materials. The term "antigen and antigenic material" which are also used interchangeably herein include one or more non-viable immunogenic or desensitizing (anti-allergic) agents of bacterial, viral or other origin, which when administered, produce a specific immunological response on the part of the host. The antigen component can consist of a dried powder, an aqueous solution, an aqueous suspension and the like, including mixtures of the same containing a nonviable immunogenic or desensitizing agent or agents.

By the term "immunostimulant" as used herein is meant a material which can be employed to potentiate non-specific immune response on the part of the host.

The composition of the present invention does not contain specific antigens per se. Rather, the composition contains only immunostimulants for producing a generalized and nonspecific immunological response on the part of the host, and further include acceptable salts, carriers, diluents, vehicles and the like for intravenous, subcutaneous or intraperitoneal administration.

Referring to the above formula I the compositions of the invention include: $R^1$ is alpha- or beta-D-1-thio-mannopyranose, or alpha- or beta-L-1-thiofucopyranose. A preferred $R^1$ substituent is where the carbohydrate is $\beta$-D-mannopyranose. The hydroxyl groups on the respective glycoside can be free or can be protected by a suitable protecting group such as acetyl, benzoyl, isopropylidene, trityl, trimethylsilyl and the like. The protecting groups can easily be removed for example by mild acid or base hydrolysis, and the like, prior to administration to the host.

$R^1$ s attached via spacer arm chain A to the steroid ring at the beta 3-position. The spacer is composed of $(CH_2)_n$ where n is 5–7 carbon atoms and preferably 6. Alternately, the spacer arm can be comprised of a chain of the formula $(CH_2)_k X (CH_2)_m$ where X is oxygen, sulfur, or NH preferably oxygen; k and m are independently 2–4 carbon atoms, preferably 2; and the sum of k and m is 4–6, preferably being 4. Representative examples of A include n-pentyl, n-hexyl, n-heptyl, $CH_2CH_2-O-CH_2CH_2-S-CH_2-S-CH_2CH_2$, $CH_2CH_2CH_2-O-CH_2CH_2$, $CH_2CH_2-O-CH_2CH_2CH_2$, $CH_2CH_2-S-CH_2CH$, $CH_2CH_2CH_2-S-CH_2CH_2CH_3$ and the like. A preferred A substituent is n-hexyl.

$R^2$ is the steroidal 17-substituent preferably being in the 17-beta position of the steroid ring. $R^2$ can be $C_1-C_8$ alkyl including linear and branched alkyl and can be methyl, ethyl, propyl, isopropyl, isobutyl, isopentyl, and the like. Preferred is where the alkyl chain is 2,6-dimethylhexyl, being the well-known 17-beta cholesterol side chain. R2 further can be $C_2-C_{10}$ alkene, including linear or branched alkenes including, vinyl, propenyl, isopropenyl, n-butenyl, isobutenyl, isopentenyl, allyl and the like. Preferred is the alkene: 2,6-dimethyl-3-ethyl-hex-4-enyl, being the 17-stigmasterol side chain.

$R^2$ can further be

where B is:
(a) $C_1-C_8$ alkyl, e.g. methyl, ethyl, propyl, isopropyl, butyl, tert-butyl, pentyl, hexyl, heptyl, octyl, isooctyl, and the like.
Preferred $C_1-C_8$ alkyl is methyl.
(b) $C_1-C_8$ alkoxy for example methoxy, ethoxy, propoxy, isopropoxy, butoxy, t-butoxy, pentyloxy, hexyloxy, and the like. Preferred is methoxy.
(c) $NR^3R^4$, where $R^3$ and $R^4$ are independently selected from hydrogen, $C_1-C_4$ alkyl, including $NH_2$, $NHCH_3$, $NHCH_2CH_3$, $NEt_2$ and the like. Preferred is where $NR^3R^4$ group is unsubstituted amino.
(d) $CHCH_3(D)$, where D is OH, $NH_2$, $NHR^5$ where $R^5$ is $C_1-C_8$ alkyl, including methyl, ethyl, propyl, isopropyl and the like. Preferred is where D is OH or $NH_2$.

Representative examples include:

6-(5-Cholesten-3β-yloxy)hexyl-1-thio-α-D-mannopyranoside;
6-(5-Cholesten-3β-yloxy)hexyl-1-thio-βD-mannopyranoside;
6-(5-Cholesten-3β-yloxy)hexyl-1-thio-β-L-fucopyranoside;
6-(2-(5-Cholesten-3β-yloxy)ethoxy)ethyl-1-thio-β-D-mannopyranoside;
6-(Stigmasta-5,22-dien-3β-yloxy)hexyl-1-thio-ββ-D-mannopyranoside;
6-(Pregn-5-en-20-one-3β-yloxy)hexyl-1-thio-β-D-mannopyranoside;
6-(17β-Carbomethoxy-androst-5-en-3β-yloxy)hexyl-1-thio-β-D-mannopyranoside;
6-(17β-Carbamido-androst-5-en-3β-yloxy)-hexyl-1-thio-β-D-mannopyranoside;
6-(Pregn-5-en-20-one-3β-yloxy)hexyl-1-thio-β-D-mannopyranoside;
6-(20S-Acetamido-pregn-5-en-3β-yloxy)-hexyl-1-thio-β-D-mannopyranoside;
6-(20R-Acetamido-pregn-5-en-3β-yloxy)-hexyl-1-thio-β-D-mannopyranoside;
6-(20S-Amino-pregn-5-en-3βB-yloxy)hexyl-1-thio-β-D-mannopyranoside; or
6-(20R-Amino-pregn-5-en-3β-yloxy)hexyl-1-thio-β-D-mannopyranoside.

Preferred is the compound 6-(5-cholesten-3β-yloxy)-hexyl-1-thio-β-D-mannopyranoside.

The compounds of the present invention can be prepared by reacting a per-O-acetyl-1-thio-glycopyranose, wherein the glycopyranose is L-fucose or D-mannose with a steroidal aglycone halide such as 6-(5-cholesten-3β-yloxy)hexyl iodide. Methods for making the per-O-acetylated thioglycopyranose are well known in the art and in general the procedure involves the reaction of an acetobromoglycose with thiourea followed by treatment of the isothiouronium salt with potassium metabisulfite which is described in the reference M. M. Ponpipom et al. Can J. Chem 58, 214 (1980) hereby incorporated by reference for this particular purpose.

Methods for producing the 6-(5-cholesten-3β-yloxy)-hexyl iodide are also well known in the art and generally involve the reaction sequence of steroidal tosylate with an alcohol which is adequately described in the reference J. C. Chabala and T. Y. Shen, Carbo Res., 67, 55 (1978), which is hereby incorporated by reference for this particular purpose. The corresponding steroids where stigmasterol, pregnenol, or androstanol are involved are formed by analogous procedures. Generally equimolar amounts of the per-O-acetylated thioglycopyranose and the steroidal hexyl iodide may be condensed in an inert, nonpolar solvent such as a halogenated solvent, e.g. dichloromethane or chloroform in the presence of a base such as e.g. triethylamine, 1,5-diazabicyclo[5.4.0]undec-5-ene or 1,5-diazabicyclo[4.3.0]non-5-ene. The reaction may be carried out from about 10° to about 30° C. under an inert atmosphere. Depending upon the base employed the reaction may take from about 0.5 hour to about a few days. Thus, when employing the above diazabicyclo compounds, the reaction is usually completed in from about 0.5 to about 3 hours, while when employing triethylamine the reaction is usually completed in about 1–3 days. Following the reaction the solution is washed with water and dried if the solvent was a halogenated solvent or if the solvent was tetrahydrofuran, the solution is evaporated to dryness and the residue is partitioned between dichloromethane and water. The dried solution is concentrated to a syrup which is put on a silica gel column and eluted with chloroform followed by 1–2% ethanol in chloroform. The desired fractions are pooled and evaporated to give the blocked product 6-(5-cholesten-3β-yloxy)hexyl per-O-acetyl-1-thio-glycopyranoside which is deblocked by basic ion exchange treatment or sodium methoxide in methanol to give the desired final product.

In general the steroid used has, as the A portion, the terminally halogenated alkoxyl group for example 6-iodohexyloxy. Further, "A" can also consist of a terminally halogenated alkoxy-alkoxy group e.g. iodoethoxyethoxy in the 3-position of the steroidal ring.

The compounds can also alternatively be synthesized by first forming the steroidal structure, in which the 17-substituent on the steroid ring is chemically blocked or is a precursor to a final product. After the condensation to form the steroidal glycopyranoside, subsequent chemistry can be carried out on the 17-group by, for example, deblocking, to form the hydroxy, reduction to form an amine, esterification to form an ester group, or de-esterification to form a carboxylic acid which can be followed by conversion to an amide or to a substituted amide or to a number carboxyl derivatives starting out originally with the ester function.

The compositions of the present invention can be conveniently prepared in an aqueous phase in a parenterally acceptable liquid. For example, the aqueous phase can be in the form of a vaccine in which the immunostimulant is dispersed in a balanced salt solution, physiological saline solution, phosphate buffered saline solution, tissue culture fluids or other media in which the organism may have been grown. The aqueous phase may also contain preservatives and or substances conventionally incorporated in vaccine preparations.

The compounds in the present invention possess immunostimulatory properties and may be used as immunomodulating agents, i.e. to stimulate the host immune response. They are especially useful for increasing the host response against viral infections.

These compounds are especially useful in the case of herpesviridae, picorna-viridae and myxo viruses, but also in the case of mastadeno viruses, such as, especially, human adeno viruses, in the case of chordopoxvirinae, such as, chiefly, orthopox viruses, such as, especially, for example, vaccinia viruses, in the case of reoviridae, above all (especially human) rota viruses, and in the case of caliciviridae and rhabdoviridae, such as, especially, vesiculo viruses in humans.

These compounds of the formula I are used chiefly in the case of alpha-herpesvirinae, such as varicella viruses, for example human varicella-zoster viruses, rhino viruses, cardio viruses and orthomyxoviridae, but also in the case of beta-herpesvirinae, such as, especially, human cytomegalo viruses, and in the case of para-myxoviridae, such as, especially, pneumo viruses, for example respiratory syncytial viruses in humans, and such as, also, morbilli viruses or para-myxo viruses, such as para-influenza viruses, for example human parainfluenza viruses, including Sendai viruses, and in the case of arbo viruses or vesiculo viruses, for example Vesicular stomatitis viruses.

These compounds are used very especially in the case of simplex viruses, for example human Herpes simplex viruses of types 1 and 2, in the case of human encephalomyocarditis viruses, in the case of influenza viruses, such as, especially, influenza A and influenza B viruses, in the case of vaccinia and para-influenza viruses and very especially in the case of the viruses mentioned in the Examples.

These compounds can be used for the prophylaxis and treatment of virus infections, by administering them enterally or parenterally, especially together with suitable adjuncts or carriers. They are preferably applied to the mucous membranes, for example intranasally, rectally or vaginally, or to the conjunctiva of the eye, or orally. However, the antiviral effect also occurs in the case of administration by other routes, for example subcutaneously, intravenously or intramuscularly, or in the case of application to normal skin.

The dosage of the active ingredient depends, inter alia, on the particular human's resistance, the method of administration and the type of virus. There is relatively little relationship between the dosage and the effect.

For prevention, a twice a day injectable dose of from approximately 40 mg/kg to approximately 80 mg/kg of body weight, preferably from 2.8 to 4.2 gm, for example 3.5 gm, of active ingredient is administered to a human of approximately 70 kg body weight. The prophylactic effect of this regimen lasts for several days. If necessary, for example when there is an increased risk of infection, the administration of this dose can be repeated.

The pharmaceutically acceptable compounds of the present invention can be used, for example, for the manufacture of pharmaceutical preparations that contain a pharmaceutically effective amount, for example an amount sufficient for immunostimulation, of the active ingredient together or in admixture with a significant amount of inorganic or organic, solid or liquid pharmaceutically acceptable carriers.

The pharmaceutical preparations according to the invention are for enteral, such as oral or rectal, and parenteral, such as intraperitoneal, intramuscular or intravenous, administration to warm-blooded animals and contain the pharmacological active ingredient alone or together with a pharmaceutically acceptable carrier.

The carriers may be inorganic or organic and solid or liquid. For example, there are used tablets or gelatine capsules that contain the active ingredient together with diluents, for example lactose, dextrose, sucrose, mannitol, sorbitol, cellulose and/or glycerine, and/or lubricants, for example silica, talc, stearic acid or salts thereof, such as magnesium or calcium stearate, and/or polyethylene glycol. Tablets may also contain binders, for example magnesium aluminium silicate, starches, such as corn, wheat or rice starch, gelatine, methylcellulose, sodium carboxymethylcellulose and/or polyvinylpyrrolidone, and, if desired, disintegrators, for example starches, agar, alginic acid or a salt thereof, such as sodium alginate, and/or effervescent mixtures, or adsorbents, colorings, flavorings and sweeteners. The pharmacologically active compounds of the present invention can also be used in the form of parenterally administrable preparations or in the form of infusion solutions. Such solutions are preferably isotonic aqueous solutions or suspensions, it being possible, for example in the case of lyophilized preparations that contain the active ingredient alone or together with a carrier, for example mannitol, for these to be manufactured before use. The mentioned solutions or suspensions may contain viscosity-increasing substances, such as sodium carboxymethylcellulose, carboxymethylcellulose, dextran, polyvinylpyrrolidone or gelatine. The pharmaceutical preparations may be sterilized and/or contain adjuncts, for example preservatives, stabilizers, wetting agents and/or emulsifiers, solubilizers, salts for regulating the osmotic pressure and/or buffers. The present pharmaceutical preparations which, if desired, may contain other pharmacologically active ingredients, such as antibiotics, are manufactured in a manner known per se, for example by means of conventional mixing, granulating, confectioning, dissolving or lyophilizing processes, and contain approximately from 0.001% to 99%, especially from approximately 0.01% to approximately 10%, more especially from 0.1% to 5%, of the active ingredient(s), an active ingredient concentration of less than 1% being especially suitable for preparations that are to be applied topically.

Pharmaceutical preparations according to the invention may be, for example, in dosage unit form, such as dragees, tablets, capsules, suppositories or ampoules.

Pharmaceutical preparations for oral administration can be obtained by combining the active ingredient with solid carriers, optionally granulating a resulting mixture and processing the mixture or granulate, if desired or necessary after the addition of suitable adjuncts, to form tablets or dragee cores. It is also possible to incorporate them into synthetic carriers that release the active ingredients, or allow them to diffuse, in a controlled manner.

The manufacture of injection preparations is carried out in customary manner under antimicrobial conditions, as is the filling into ampoules or phials and the sealing of the containers.

Furthermore, the compounds of the present invention provide, in combination with "anti-AIDS drugs", human host protection against opportunistic infections in individuals immunocompromised by an AIDS-related infectious organisms. These include fungal, viral and bacterial, including the specific conditions of Kaposi's sarcoma and pneumocystis pneumonia. They are also capable of potentiating antibiotic activity.

By the term "anti-AIDS drugs" is meant therapeutic drugs which are thought to act directly or indirectly against the AIDS-related virus by a variety of known or unknown mechanisms.

The following anti-AIDS drugs are currently being investigated and are known to exhibit either some antiviral or immunomodulating effect in a human host against the AIDS-related virus (from *Chemical & Engineering News*, Dec. 8, 1986, pp 7-14, hereby incorporated by reference for this purpose):

AL 721. Lipid mixture composed of neutral glycerides, phosphatidylcholine, and phosphatidylethanolamine in 7:2:1 ratio. Interferes with HIV infectivity but not by inhibiting reverse transcriptase; possibly it disrupts the virus's membrane. No adverse effects observed during a six-week clinical trial.

Ampligen. Mismatched double-stranded RNA polynucleotide that induces the body to release interferon, thus stimulating antiviral activity. Reportedly does not have side effects of interferon injections. Currently undergoing preliminary clinical trials in AIDS patients.

Ansamycin (rifabutin, $C_{45}H_{29}N_4O_{11}$). Italian antibacterial drug, a member of the rifamycin group of antibiotics, which are characterized by a natural ansa structure (chromophoric naphthohydroquinone group spanned by a long aliphatic bridge). Drug has shown some efficacy in treating AIDS patients with an opportunistic infection caused by the bacterium *Mycobacterium avium-intracellulare*.

Azidothymidine (AZT, 3'-azido-3'-deoxythymidine).

First drug to show promise in prolonging lives of patients with AIDS or AIDS-related complex (ARC). Well absorbed orally and effectively penetrates central nervous system, but has relatively short half-life in the body and some toxicity, with anemia and headaches. ARC patients treated with AZT showed virtually no toxic effects.

Azimexon. Cyanaziridinyl immune modulator. Early trial showed improvements in symptoms and immune function in patients with ARC but not AIDS; only toxic effect was mild hemolysis (disintegration of red blood cells with release of hemoglobin), which disappeared when treatment ceased.

Cyclosoporine (cyclosporin A). Cyclic oligopeptide with potent immunosuppressive effects, used in cancer therapy. Inhibits T4 lymphocyte-dependent immune responses. Basis of controversial AIDS therapy in France; rationale is that HIV infects "activated" T4 cells, which are primed to defend that body, so drug that prevents activation of T4 cells may limit progression of disease. The French claim encouraging results with it.

Foscarnet (trisodium phosphonoformate). Swedish drug that has been used to treat CMV infection in immunocompromised patients, also to treat herpes. Inhibits HIV reverse transcriptase activity in vitro at levels pharmacologically acceptable in vivo. Formulation problems and serious side effects have been encountered. No results yet reported in HIV-infected patients.

HPA-23 (ammonium 21-tungsto-9-antimoniate, $[(NH_4)_{18}(NaW_{21}Sb_9O_{86})_{17}]$. Inhibits reverse transcriptase in several retroviruses in vitro, but mechanism of antiviral action against HIV is unknown. Drug has shown some tendency to check the growth of HIV, but no therapeutic benefit has been documented in AIDS patients.

Imreg-1. Proprietary immunemodulator derived from white blood cells. Reportedly can enhance production of other biological response modifiers such as interleukin-2 and $\gamma$-interferon, which are critical to normal functioning of immune system.

Inosine pranobex (isoprinosine, inosiplex). p-Acetamidobenzoic acid salt of (1-dimethyl amino-2-propanol:inosinate complex 3:3:1 molar ratio). Chemically synthesized antiviral and immune modulator originally developed to enhance memory in elderly. In one study, found to improve immune function in ARC patients.

$\alpha$-Interferon. Glycoprotein produced by cells in response to virus infection; helps amplify or regulate immune responses. Checks the growth of HIV in vitro. Has induced tumor regression in some AIDS-related Kaposi's sarcoma cases. Not known whether $\alpha$-interferon has anti-HIV activity in vivo.

Interleukin-2 (IL-2). Protein made by white blood cells that mediates production of interferon. Inability to produce IL-2 may predispose AIDS patients to opportunistic infections. Preliminary results of therapy with recombinant IL-2 not encouraging, but trials continue.

D-Penicillamine (3-mercapto-D-valine). Used to treat rheumatoid arthritis and Wilson's disease, a rare copper-storage disease. Inhibits HIV reproduction in humans. In trials at George Washington University Medical Center, it suppressed the virus but also temporarily depressed T cell levels in 13 AIDS patients with perpetually swollen glands.

Ribavirin (1-$\beta$-D-ribofuranosyl-1,2,4-triazole-3-carboxamide). Synthetic nucleoside used to treat a viral respiratory infection in children. In early clinical trials, it inhibited viral replication and improved immune function in AIDS patients. Longer (24-week) trial in 373 ARC patients was completed last month; at 12 weeks, ribavirin's safety profile was judged to be acceptable, and the drug was found to be well tolerated. Final results will be available soon.

Suramin ($C_{51}H_{34}Na_6O_{23}S_6$). Antiparasitic agent. Potent inhibitor of HIV reverse transcriptase, but also significantly inhibits desirable biological functions. In AIDS patients, it has produced little or no evidence of clinical improvement or immunologic recovery. Has serious side effects, inability to penetrate central nervous system. Not considered appropriate for single-agent use in AIDS. No longer being actively pursued.

Furthermore, the U.S. Food and Drug Administration has released a list of 16 proposed AIDS treatments which have received IND status. The list contains only treatments which "have been publicly acknowledged by their sponsors", and therefore some experimental treatments may have been omitted.

| Experimental treatment | Sponsor |
|---|---|
| Immunomodulators | |
| Thymopentin | Ortho Pharmaceuticals |
| Thymostimulin | Serono Laboratories |
| Methionine-enkephalin | National Jewish Hospital |
| Isoprinosine | Newport Pharmaceuticals |
| Antivirals | |
| Ansamycin | Adria Laboratories |
| Ribavirin | Viratek/ICN Pharmaceuticals |
| Dideoxycytidine (DDC) | National Cancer Institute |
| HPA-23 | Rhone-Poulenc |
| AL-721 | Matrix Laboratories[1] |
| Foscarnet | National Institute of Allergy and Infectious Diseases[2] |
| Biologicals | |
| Alpha-interferon | Hoffmann-La Roche |
| Gamma-interferon | Genentech |
| Imreg-1 | Imreg Inc |
| Interleukin-2 | Hoffmann-La Roche |
| RNA deriv | HEM Research |
| Immune globulin IG-IV | Sandoz Pharmaceuticals and Alpha Therapeutics |

[1] a subsidiary of Praxis Pharmaceutical;

Further, Yakult's immunostimulant, LC-9018, and two herbal products, shosaikoto and ginseng, being studied by Tsumura Juntendo, may be of benefit in patients with AIDS, according to a recent note from Jardine Fleming analysts (Japan).

LC-9018 has been found to be about 20 times more potent than Ajinomoto's lentinan in inducing macrophage activation, and it will soon enter clinical trials in AIDS patients in the U.S., note the analysts. Phase III trials with LC-9018 in patients with cancer are currently underway in Japan, they add. Shosaikoto and ginseng have been found to increase depleted helper T-cell counts in seven of nine AIDS-carriers studied by researchers at Tsumura Juntendo and Tokyo Medical University, the Jardine Fleming analysts note.

Furthermore, HEM Research's potential anticancer agent, ampligen (a mismatched double-stranded RNA), reduces at least five-fold the concentration of Wellcome's zidovudine (Retrovir) required for inhibitory activity against human immunodeficiency virus (HIV) in vitro, according to U.S. researchers writing in *The Lancet* (April 18th, p 890). Ampligen is currently in Phase II clinical trials as an anticancer agent and HEM is seeking partners to fund a clinical trial in AIDS.

At higher concentrations of zidovudine, there seemed to be a synergistic relation between the two compounds, since complete protection was provided by combined suboptimal doses of each drug, the authors note. They predict that ampligen would reduce the dose of zidovudine required for a therapeutic effect in vivo, so reducing its toxicity.

Since the two drugs have entirely different modes of action, it is unlikely that they will exert toxicities other than those associated with each drug alone, the researchers comment. In recent clinical studies, "virtually no toxicity" was associated with intravenous ampligen, they add. Moreover, since ampligen has clinically demonstrated immunological as well as antiviral activity, its use together with zidovudine may have pronounced and long-term beneficial effects on the course of AIDS beyond that which can be estimated in vitro, they conclude.

In addition, CS-85, or 3'-azido-2',3'-dideoxy-5-ethyl-(uridine) developed by Raymond F. Schinozi at the Veterans Administration Medical Center and Emory University, both in Atlanta, Ga., shows promise.

All of the above-described compounds are deemed to be included within the scope of the term "anti-AIDS drug" as used herein. Use of more than one of these compounds, in addition to the glyocolipid of structure I, in the combination composition is contemplated.

The composition containing the glycolipid compounds and an above-described anti-AIDS drug will contain the glycolipid in an amount as described above and the anti-AIDS drug in an amount, based on the glycolipid, in a weight ratio of 1:3 to 3:1 and preferably 1:1 based on the weight of glycolipid.

The dosage form of the combination drug will be 1 to 50 mg/kg of human body weight per day and preferably 2.5 to 40 mg/kg.

The method of co-administering the two ingredients, if not using the combination composition can be separately, concurrently or simultaneously.

The obtained compounds can be transformed to their salts in a classical fashion, for example, by reacting the acidic compounds obtained with alkaline or alkaline earth hydroxides or the basic compounds with acids.

The present invention is also directed to pharmaceutical preparations that contain a compound of Formula II. Among the pharmaceutical preparations relevant to this invention are salts that are administered by external route, for example, orally, rectally or parenterally to human species. Preparations may be administered that contain the pharmacologically active compound by itself or mixed with a pharmacologically acceptable carrier. The dose of the pharmacologically active compound depends on the sex, the age, and the state of the human individual and the mode of application.

The new pharmaceutical preparations contain from about 10% to about 95% and, preferably from about 20% to about 90% of a compound of the present invention. The pharmaceutical preparation relevant to this invention can be presented, for example, in the form of unit doses like tablets, capsules, suppositories, and ampoules.

A further characteristic of the composition is in that the compounds which are present for their immunostimulatory response preferably are in their noncrystalline form. For reasons which are not yet known or clear, when the materials are present in the crystal form they appear to be less active in producing an immunological response generalized to the same degree as the materials would have produced in the amorphous form. The crystallinity of the sample can easily be determined by X-ray diffraction analysis which should indicate the absence of a peak height pattern but simply background noise indicating an amorphous material.

Also a subject of the invention is a method for administering to an immunocompromised host a composition as described herein, containing a compound of the formula I, as described, contained in a suitable carrier which may or may not have additional material such as diluents and other materials which may be deemed necessary under the circumstances. However, it is understood that the immunostimulatory preparation does not in fact include a specific antigen as a composition component.

The following examples exhibit the subject invention as contemplated by us and should not be construed as being limited with respect to the scope and nature of the instant invention.

EXAMPLE 1

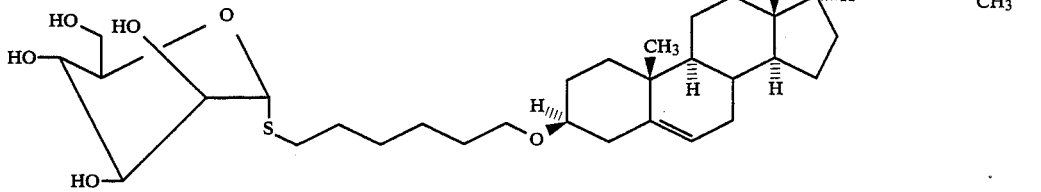

6-(5-Cholesten-3β-yloxy)hexyl 1-thio-α-D-mannopyranoside

Prepared from 2,3,4,6-tetra-O-acetyl-1-thio-α-D-mannopyranoside and cholest-5-en-3β-yl 6-iodohexyl ether as described in the literature. [Chabala, J. C. and Shen, T. Y., Carbohydr. Res., 67 (1978) 55–63].

Step A: Cholest-5-en-3β-yl 6-hydroxyhexyl ether

By use of the procedure described in the literature [Kosower, E. M. and Weinstein, S., J. Am. Chem. Soc., 78 (1956) 4347–4354; Davis, M., J. Chem. Soc., (1962) 178–181] cholesteryl p-toluenesulfonate and 1,6-hexanediol were condensed in boiling dioxane to give cholest-5-en-3β-yl 6-hydroxyhexyl ether in 52% yield as colorless plates (from hexane), m.p. 75.9°–81° C.

Step B: Cholest-5-en-3β-yl 6-(p-toluenesulfonyloxy)hexyl ether

A solution of cholest-5-en-3β-yl 6-hydroxyhexyl ether (32 g, 66 mmol) in dry benzene (1.3 L) was treated with p-toluenesulfonic anhydride (24 g, 72.6 mmol) and 2,4,6-trimethylpyridine (11.6 ml, 8.8 g, 72 mmol), and stirred at room temperature under a dry nitrogen atmosphere for 1 hour. The mixture was filtered through a pad of Florisil and concentrated to a waxy solid (33 g, 77%).

Step C: Cholest-5-en-3β-yl 6-iodohexyl ether

A solution of cholest-5-en-3β-yl 6-(p-toluenesulfonyloxy)hexyl ether (33 g, 51 mmol) and sodium iodide (16 g, 0.106 mol) in acetone (250 ml) was refluxed for 4 hours. The solvent was removed under reduced pressure, filtered, and the collected salts washed well with ether. The filtrate was evaporated and residual yellow oil boiled in hexanes (400 ml). The solution was decanted, concentrated to 200 ml, and stored in the refrigerator for two days. The product was filtered and the mother liquors concentrated to give a total yield of 30 g (97%), m.p. 103.5°–104.5° C.

Step D: 6-(5-Cholesten-3β-yloxy)hexyl 1-thio-α-D-mannopyranoside

To a solution of 2,3,4,6-tetra-0-acetyl-1-thio-α-D-mannopyranose (287 mg, 0.79 mmol) in dichloromethane (6 ml) was added cholest-5-en-3β-yl 6-iodohexyl ether (470 mg, 0.79 mmol) and triethylamine (0.11 ml, 0.79 mmol). After stirring under dry nitrogen atmosphere overnight at room temperature, the solvent was removed at reduced pressure and the residue chromatographed on silica gel eluted with 5–25% ethyl acetate in hexanes to give 6-(cholest-5-en-3β-yloxy)hexyl 2,3,4,6-tetra-O-acetyl-1-thio-α-D-mannopyranoside (0.36 g, 55% yield), m.p. 103°–103.5° C. This product was dissolved in 1:1 (v/v) ethanol-tetrahydrofuran (10 ml) and treated with a suspension of Bio-Rad AG—1—X2 OH— ion-exchange resin (2.5–3 fold excess) in ethanol (5 ml). After stirring a room temperature for 45 minutes, the resin was filtered and washed with warm tetrahydrofuran (3×5 ml), and the combined filtrates concentrated to give 6-(5-cholesten-3β-yloxy)hexyl 1-thio-α-D-mannopyranoside (250 mg, 91% yield) as needles from warm tetrahydrofuran, m.p. (endothermic transitions) 64°–64°, 81°–82°, and 226°–227° C.

EXAMPLE 2

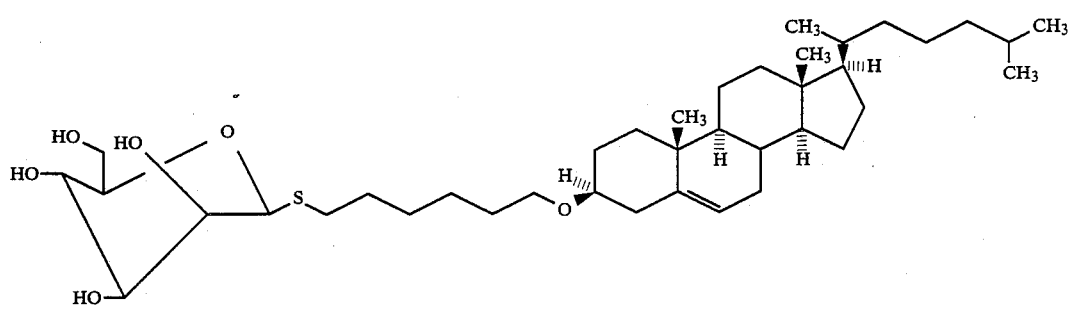

6-(5-Cholesten-3β-yloxy)hexyl 1-thio-β-D-mannopyranoside

A solution of the sodium salt of 1-thio-β-D-mannopyranoside [prepared by the procedure of Tejima, S. et al., Chem. Pharm. Bull. Jap., 12 (1964) 528–532] (2.0 g, 9.1 mmol) in water (8 ml) was added to a solution of cholest-5-en-3β-yl 6-iodohexyl ether (6.0 g, 10.0 mmol) in tetrahydrofuran (40 ml) under nitrogen atmosphere. After stirring at room temperature for 24 hours, the solvent was removed by rotoevaporation and the resultant solid mass was purified by flash column chromatography [Still, W. C. et al., J. Org. Chem., 43 (1978) 2923–2925] on silica gel eluted with chloroform to 5%–10% methanol/chloroform. The eluent solvent was removed by evaporation to give 6-(5-cholesten-3β-yloxy)hexyl 1-thio-β-D-mannopyranoside as a white powder (6.2 g).

The reaction product was chromatographed by thin layer chromatography (TLC) on Analtech Silica Gel GHLF 250 micron plates in 10% methanol/chloroform. The resulting $R_f$ value is given below in the Table 1.

TABLE I

| Example No. | Thin Layer Chromatography Values for Examples | |
|---|---|---|
| | Rf Value | Solvent System* |
| 1 | Cited from literature. | |
| 2 | 0.54 | A |
| 3 | Not run. | |
| 4 | Cited from literature. | |
| 5A | 0.68 | B |
| 5B | 0.48 | C |
| 5C | 0.82 | C |
| 5D | Not run | — |
| 6A | 0.46 | D |
| 6B | 0.87 | D |
| 6C | 0.32 | E |
| 6D | 0.26 | A |
| 7A | 0.27 | D |
| 7B | 0.56 | D |
| 7C | 0.59 | C |
| 7D | 0.28 | A |
| 8A | 0.11 | C |
| 8B | 0.35 | C |
| 8C | 0.66 | F |
| 8D | 0.17 | A |
| 9A | 0.44 | G |
| 9B | 0.61 | G |
| 10 | 0.54 | G |
| 11A | 0.56 | C |
| 11B | 0.15 (S), 0.29 (R) | A |
| 11C | 0.10 | H |
| 11D | 0.12 | B |
| 11E | 0.56 | G |
| 12C | 0.20 | H |
| 12D | 0.81 | G |
| 12E | 0.60 | G |
| 13A | 0.23 | F |
| 13B | 0.69 | B |
| 13C | 0.50 | C |
| 13D | 0.20 | A |
| 13E | 0.18 | G |
| 14A–E | Not run | — |

*Solvent Systems:
A - 10% methanol/chloroform
B - 50% ethyl acetate/hexanes
C - 25% ethyl acetate/hexanes
D - 30% ethyl acetate/hexanes
E - 10% ether/hexanes
F - 10% ethyl acetate/hexanes
G - 80:22:2; chloroform:methanol:water
H - 75% ethyl acetate/hexanes

EXAMPLE 3

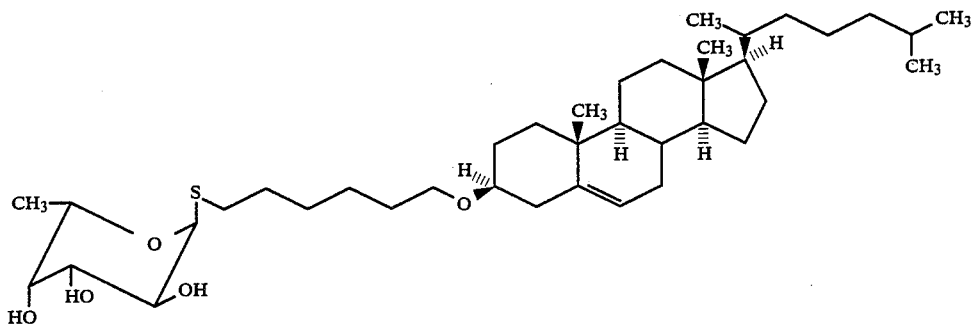

6-(5-Cholesten-3β-yloxy)hexyl
1-thio-α-L-fucopyranoside

Employing the procedure substantially as described in Example 2, but substituting for the sodium salt of 1-thio-β-D-mannopyranose, an equivalent amount of the sodium salt of 1-thio-α-L-fucopyranose, this compound is prepared.

EXAMPLE 4

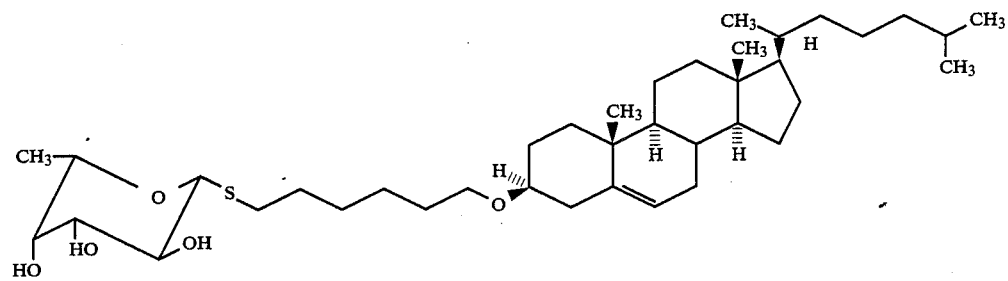

6-(5-Cholesten-3β-yloxy)hexyl
1-thio-β-L-fucopyranoside

The title compound was prepared from 2,3,4,6-O-tetra-acetyl-1-thio-β-L-fucopyranose and cholest-5-en-3β-yl 6-iodohexyl ether as described in Ponpipom, M. M. et al., Can. J. Chem., 58 (1980) 214–220.

EXAMPLE 5

2-(2-(5-Cholesten-3β-yloxy)ethoxy)ethyl
1-thio-β-D-mannopyranoside

Employing the procedure substantially as described in Example 1, but substituting for 1,6-hexanediol, used in the preparation of cholest-5-en-3-yl 6-iodohexyl ether thereof, an equivalent amount of diethylene glycol, there was prepared in sequence:

Step A: 2-(2-(5-Cholesten-3β-yloxy)ethoxy)ethanol
Step B: 2-(5-Cholesten-3β-yloxy)ethyl 2-(p-tolyl sulfonyloxy)ethyl ether
Step C: 2-(5-Cholesten-3β-yloxy)ethyl 2-iodoethyl ether Employing the procedure substantially as described in Example 2, but substituting for cholest-5-en-3-yl 6-iodohexyl ether, an equivalent amount of 2-(5-cholesten-3-yloxy)ethyl 2-iodoethyl ether, there was produced 2-(2-(5-Cholesten-3β-yloxy)ethyl)ethyl 1-thio-β-D-mannopyranoside (Step D). TLC data and $R_f$ values are given in the above Table.

EXAMPLE 6

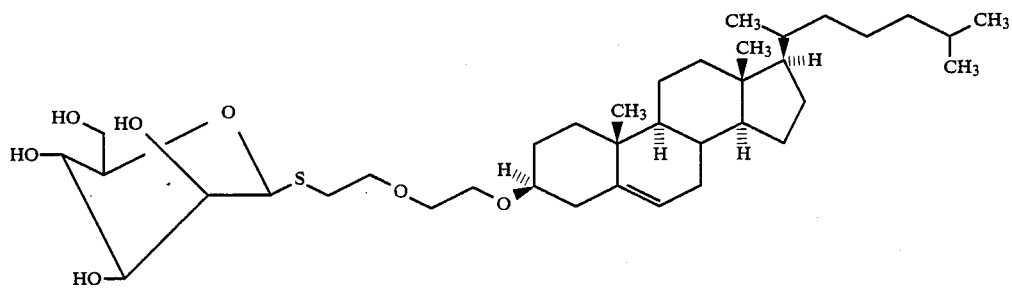

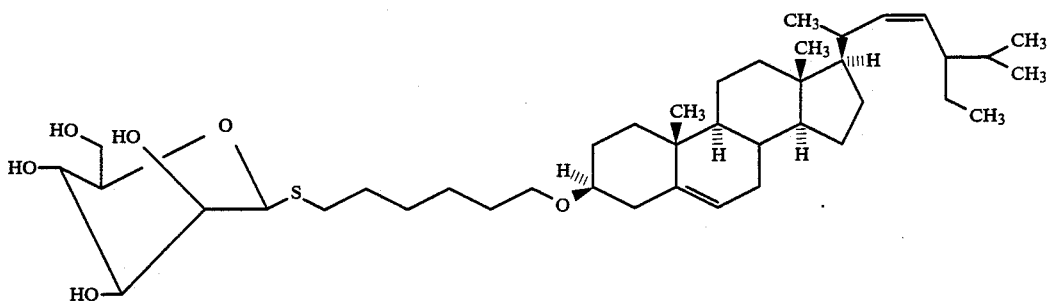

6-(Stigmasta-5,22-dien-3β-yloxy)hexyl
1-thio-β-D-mannopyranoside

Employing the procedure substantially as described in Example 1, but substituting for cholest-5-en-3β-yl, used in the preparation of cholest-5-en-3β-yl 6-iodohexyl ether, an equivalent amount of stigmasta-5,22-dien-3β-yl p-toluenesulfonate, there was prepared in sequence:

Step A: Stigmasta-5,22-dien-3β-yl 6-hydroxyhexyl ether
Step B: Stigmasta-5,22-dien-3β-yl 6-(p-tolylsulfonyloxy)hexyl ether
Step C: Stigmasta-5,22-dien-3β-yl 6-iodohexyl ether Employing the procedure substantially as described in Example 2, but substituting for cholest-5-en-3β-yl 6-iodohexyl ether, an equivalent amount of stigmasta-5,22-dien-3β-yl 6-iodohexyl ether, there was prepared 6-(stigmasta-5,22-dien-3β-yloxy)hexyl 1-thio-β-D-mannopyranoside (Step D). TLC data and $R_f$ values are given in the above Table.

EXAMPLE 7

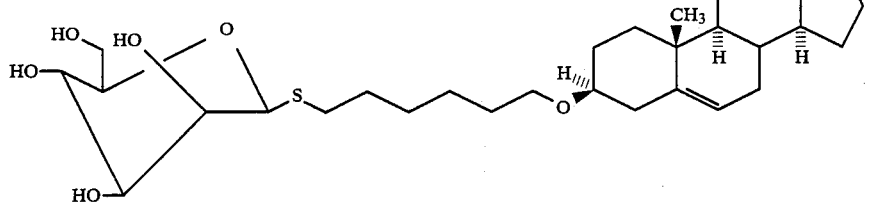

6-(Pregn-5-en-20-one-3β-yloxy)hexyl
1-thio-β-D-mannopyranoside

Employing the procedure substantially as described in the literature [see Example 1], but substituting for cholesteryl p-toluenesulfonate used in the preparation of cholest-5-en-3β-yl 6-iodohexyl ether, an equivalent amount of 5-pregnen-20-one-3β-yl p-toluenesulfonate, there was prepared in sequence:

Step A: Pregn-5-en-20-one-3β-yl 6-hydroxyhexyl ether
Step B: Pregn-5-en-20-one-3β-yl 6-(p-tolylsulfonyloxy)hexyl ether
Step C: Pregn-5-3n-20-one-3β-yl 6-iodohexyl ether Employing the procedure substantially as described in Example 2, but substituting for cholest-5-en-3β-yl 6-iodohexyl ether, an equivalent amount of pregn-5-en-20-one-3β-yl 6-iodohexyl ether, there was prepared 6-(Pregn-5-en-20-one-3β-yloxy)hexyl 1-thio-β-D-mannopyranoside (Step D). TLC data and $R_f$ values are given in the above Table.

EXAMPLE 8

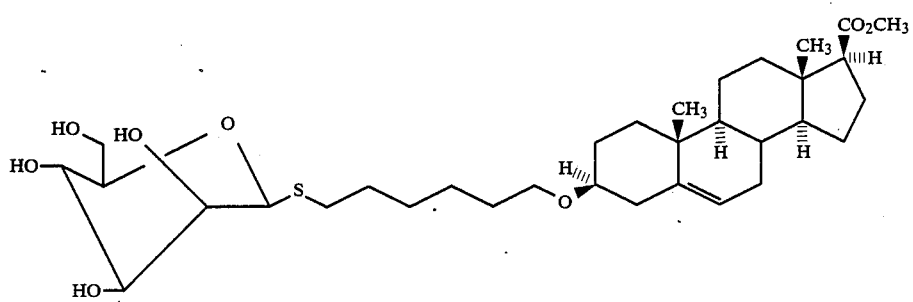

6-(17β-Carbomethoxy-androst-5-en-3β-yloxy)hexyl
1-thio-β-D-mannopyranoside

Employing the procedure substantially as described in the literature [see Example 1], but substituting for cholesteryl p-toluenesulfonate used in the preparation of cholest-5-en-3β-yl 6-iodohexyl ether, an equivalent amount of 17β-carbomethoxy-androst-5-en-3β-yl p-toluenesulfonate, there was prepared in sequence:

Step A: 17β-Carbomethoxy-androst-5-en-3β-yl 6-hydroxyhexyl ether

Step B: 17β-Carbomethoxy-androst-5-en-3β-yl 6-(p-tolylsulfonyloxy)hexyl ether

Step C: 17β-Carbomethoxy-androst-5-en-3β-yl 6-iodohexyl ether

Employing the procedure substantially as described in Example 2, but substituting for cholest-5-en-3β-yl 6-iodohexyl ether, an equivalent amount of 17β-carbomethoxy-androst-5-en-3β-yl 6-iodohexyl ether, there was prepared 6-(17β-carbomethoxy-androst5-en-3β-yloxy)-hexyl 1-thio-β-D-mannopyranoside (Step D). TLC data and R$_f$ values are given in the above Table.

EXAMPLE 9

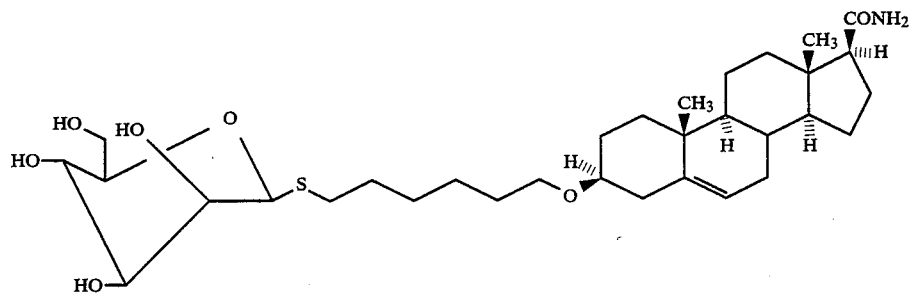

6-(17β-Carbamido-androst-5-en-3β-yloxy)hexyl 1-thio-β-D-mannopyranoside

Step A: 6-(17β-Carboxyl-androst-5-en-3β-yloxy)hexyl 1-thio-β-D-mannopyranoside

A solution of 6-(17β-carbomethoxy-androst-5-en-3β-yloxy)hexyl 1-thio-β-D-mannopyranoside (550 mg) and potassium hydroxide (85%, 110 mg) in methanol (1.4 ml) and water (0.3 ml) was refluxed for 29 hours under a nitrogen atmosphere. After cooling, 6N hydrochloric acid (3 ml) was added and the suspension filtered. The white solid was successively washed with water (5×) and dried to give the carboxylic acid (316 mg). The 200 MHz NMR spectrum in chloroform-d and the infra-red spectrum of the peracetylated derivative was in accord with the desired structure.

Step B: 6-(17β-Carbamido-androst-5-en-3β-yloxy)hexyl 1-thio-β-D-mannopyranoside

A solution of 6-(17β-carboxyl-androst-5-en-3β-yloxy)hexyl 1-thio-β-D-mannopyranoside (425 mg) in chloroform (2 ml) and toluene (2 ml) at 0° C. was treated with pyridine (0.5 ml) and oxalyl chloride (0.5 ml). After stirring at room temperature for 2 hours, the solution was added to a solution of chloroform saturated with ammonia gas. After stirring at room temperature for 2 hours, chloroform (150 ml) was added and the solution successively washed with water (3×) and dried over anhydrous sodium sulfate. The solvent was removed by rotoevaporation to give the product as a slightly orange powder. The 200 MHz NMR spectrum in chloroform-d of the peracetylated derivative was in accord with the desired structure. TLC data and R$_f$ values given in the above Table.

EXAMPLE 10

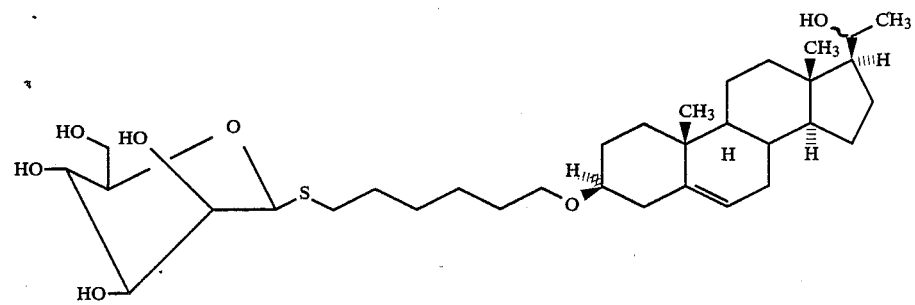

6-(Pregn-5-en-20-ol-3β-yloxy)hexyl 1-thio-β-D-mannopyranoside

Sodium borohydride (60 mg) was added to a solution of 6-(pregn-5-en-20-one-3β-yloxy)hexyl 1-thio-β-D-mannopyranoside (250 mg) in absolute ethanol (7 ml). After stirring at room temperature for 4 hours, the solution was cooled and glacial acetic acid (10 ml) was slowly added. The solution was added to chloroform (100 ml) and successively washed with water (3×), 1N sodium bicarbonate (2×), and water (1×) and dried over anhydrous sodium sulfate. The solvent was removed by rotoevaporation to give the product as a fine white solid. The 200 MHz NMR spectrum of the peracetylated derivative was in accord with the desired structure. TLC data and R$_f$ values are given in the above Table.

EXAMPLE 11

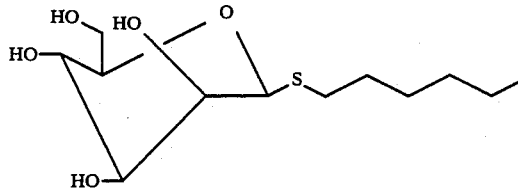

6-(20S-Acetamido-pregn-5-en-3β-yloxy)hexyl 1-thio-β-D-mannopyranoside

Step A: Pregn-5-en-20-one-3β-yl 6-(2-tetrahydropyranyloxy)hexyl ether

A solution of pregn-5-en-20-one-3β-yl 6-hydroxyhexyl ether (6.22 g) and p-toluenesulfonic acid (20 mg) in dihydropyran (100 ml) was stirred at room temperature for 18 hours. Solid sodium bicarbonate (1 g) was added and the mixture stirred for 30 minutes. The mixture was filtered through a pad of silica gel which was subsequently washed with 50% ethyl acetate in hexanes. The solvent was removed by rotoevaporation to give the product as a clear colorless oil. TLC data and $R_f$ values for compounds A–D are given in the above Table.

Step B: 20R-and 20S-Amino-pregn-5-en-3β-yl 6-(2-tetrahydropyranyloxy)hexyl ether Employing the Procedure substantially as described in the literature [Lu, M. T., et al., *J. Med. Chem.*, 15 (1972) 1284], but substituting for 3β-acetoxy-pregn-5-en-20-one in the preparation of 3β-acetoxy-20-amino-pregn-5-ene, an equivalent amount of pregn-5-en-20-one-3β-yl 6-(2-tetrahydropyranyloxy)hexyl ether, there was prepared in sequence: (1) 20-Oximo-pregn-5-en-3β-yl 6-(2-tetrahydropyranyloxy)hexyl ether and (2) 20R,S-Amino-pregn-5-en-3β-yl 6-(2-tetrahydropyranyloxy)hexyl ether. This mixture of diastereomers was separated into its respective 20R- and 20S-amino compounds by HPLC on silica gel eluted with 15% methanol in chloroform.

Step C: 20S-Acetamido-pregn-5-en-3β-yl 6-hydroxyhexyl ether

A solution of 20S-amino-pregn-5-en-3β-yl 6-(tetrahydropyranyloxy)hexyl ether (23 g) in pyridine (50 ml) and acetic anhydride (30 ml) was stirred at room temperature for 6 hours. The solvent was removed by rotoevaporation at high vacuum to give 20S-acetamido-pregn-5-en-3β-yl 6-(2-tetrahydropyranyloxy)hexyl ether which was subsequently dissolved in tetrahydrofuran (50 ml) and methanol (100 ml). Dowex 50W-8X (H+form, 25 g) was added and the mixture stirred for 48 hours. The resin was filtered and the solvent removed by rotoevaporation to give 20S-acetamido-pregn-5-en-3β-yl 6-hydroxyhexyl ether.

Step D: 20S-Acetamido-pregn-5-en-3β-yl 6-iodohexyl ether

Employing the procedure substantially as described in the literature [see Example 1], but substituting for cholest-5-en-3β-yl 6-hydroxyhexyl ether in the preparation of cholest-5-en-3β-yl 6-iodohexyl ether, an equivalent amount of 20S-acetamido-pregn-5-en-3β-yl 6-hydroxyhexyl ether, there was prepared 20S-acetamido-pregn-5-en-3β-yl 6-(p-tolylsulfonyloxy)hexyl ether and 20S-acetamido-pregn-5-en-3β-yl 6-iodohexyl ether.

Step E: 6-(20S-Acetamido-pregn-5-en-3β-yloxy)hexyl 1-thio-β-D-mannopyranoside Employing the procedure substantially as described in Example 2, but substituting for cholest-5-en-3β-yl 6-iodohexyl ether, an equivalent amount of 20S-acetamido-pregn-5-en-3β-yl 6-iodohexyl ether, there was prepared 6-(20S-acetamido-pregn-5-en-3β-yloxy)hexyl 1-thio-β-D-mannopyranoside.

EXAMPLE 12

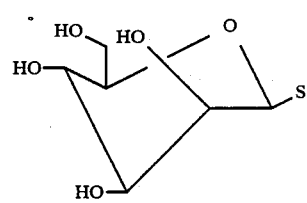

6-(20R-Acetamido-pregn-5-en-3β-yloxy)hexyl 1-thio-β-D-mannopyranoside

Employing the procedure substantially as described in Example 10, Steps C through E, but substituting for 20S-acetamido-pregn-5-en-3β-yl 6-(2-tetrahydropyranyloxy)hexyl ether, an equivalent amount of 20R-acetamido-Pregn-5-en-3β-yl 6-(2-tetrahydropyranyloxy)hexyl ether, there was prepared in sequence:

Step C: 20R-Acetamido-pregn-5-en-3β-yl 6-hydroxyhexyl ether
Step D: 20R-Acetamido-pregn-5-en-3β-yl 6-iodohexyl ether
Step E: 6-(20R-Acetamido-pregn-5-en-3β-yloxy)hexyl 1-thio-β-D-mannopyranoside TLC data and R$_f$ values for compounds C–E are given in the above Table.

EXAMPLE 13

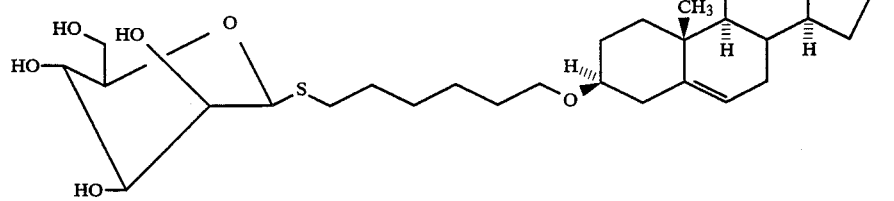

6-(20R-Amino-pregn-5-en-3β-yloxy)hexyl 1-thio-β-D-mannopyranoside

Step A:
N-(2,2,2-trichloro-ethoxycarbonyl)-20R-amino-pregn-5-en-3β-yl 6-(2-tetrahydropyranyloxy)hexyl ether To a solution of 20R-amino-pregn-5-en-3β-yl 6-(2-tetrahydropyranyloxy)hexyl ether [see Example 11, Step B] (1.2 g) in pyridine (5 ml) under a dry nitrogen atmosphere was added 2,2,2-trichloro-ethoxycarbonyl chloride (1 ml). After stirring at room temperature for 6 hours, chloroform (100 ml) was added and the solution was washed successively with 1N hydrochloric acid (3×, 1N sodium bicarbonate solution (2×). The solution was dried over anhydrous sodium sulfate and the solvent removed by rotoevaporation to give the product. TLC data and R$_f$ values for compounds A–E are given in the above Table.

Step B:
N-(2,2,2-trichloro-ethoxycarbonyl)-20R-amino-pregn-5-en-3⊖-yl 6-hydroxyhexyl ether A solution of N-(2,2,2-trichloro-ethoxycarbonyl)-20R-amino-pregn-5-en-3β-yl 6-(2-tetrahydropyranyloxy)hexyl ether (1.6 g) in methanol (10 ml) containing Dowex 50W-8X (H+form, 3 g) was stirred at room temperature for 34 hours. Ethyl acetate (100 ml) was added, the mixture filtered, and the solution washed successively with 1N sodium bicarbonate solution (3×) and water (2×). After drying over anhydrous sodium sulfate, the solvent was removed by rotoevaporation to give the product.

Step C:
N-(2,2,2-Trichloro-ethoxycarbonyl)-20R-amino-pregn-5-en-3β-yl 6-iodohexyl ether Employing the procedure substantially as described in the literature [see Example 1], but substituting for cholest-5-en-3β-yl 6-hydroxyhexyl ether in the preparation of cholest-5-en-3β-yl 6-iodohexyl ether, an equivalent amount of N-(2,2,2-trichloro-ethoxycarbonyl)-20R-amino-pregn-5-en-3β-yl 6-hydroxyhexyl ether, there was prepared this compound.

Step D:
6-(N-(2,2,2-Trichloro-ethoxycarbonyl)-20R-amino-pregn-5-en-3β-yloxy)hexyl 1-thio-β-D-mannopyranoside Employing the procedure substantially as described in Example 2, but substituting for cholest-5-en-3β-yl 6-iodohexyl ether, an equivalent amount of N-(2,2,2-trichloro-ethoxycarbonyl)-20R-amino-pregn-5-en-3β-yl 6-iodohexyl ether, there was prepared this compound.

Step E: 6-(20R-Amino-pregn-5-en-3β-yloxy)hexyl 1-thio-β-D-mannopyranoside

To a solution of 6-(N-(2,2,2-trichloro-ethoxycarbonyl)-20R-amino-pregn-5-en-3β-yloxy)hexyl 1-thio-β-D-mannopyranoside (2.7 g) in glacial acetic acid (10 ml) was added in portions zinc dust (3.4 g) over a 70 hour period. Tetrahydrofuran (100 ml) and methanol (20 ml) were added and the mixture was filtered. The solvent was removed by rotoevaporation and the residue dissolved in methanol (50 ml) to which was added solid sodium bicarbonate (5 g). After stirring for 15 minutes, the mixture was filtered and the solvent removed by rotoevaporation. The residue was purified by flash column chromatography on silica gel eluted with 10%–20% methanol in chloroform to give this compound.

EXAMPLE 14

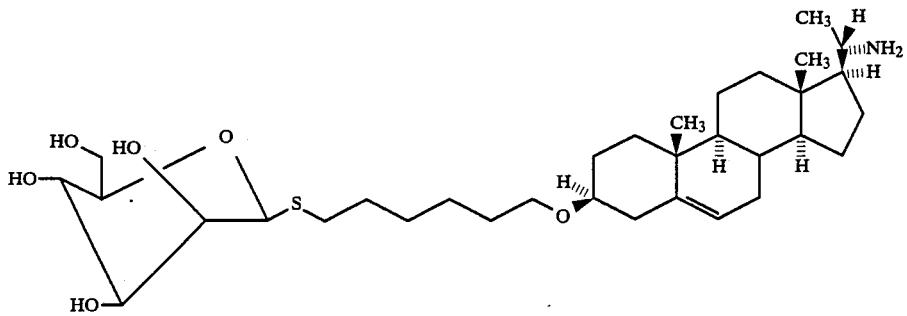

6-(20S-Amino-pregn-5-en-3β-yloxy)hexyl 1-thio-β-D-mannopyranoside

Employing the procedure substantially as described in Example 13, but substituting for 20R-amino-pregn-5-en-3β-yl 6-(2-tetrahydropyranyloxy)hexyl ether, an equivalent amount of 20S-amino-pregn-5-en-3β-yl 6-(2-tetrahydropyranyloxy)hexyl ether, there was prepared in sequence:

Step A: N-(2,2,2-trichloro-ethoxycarbonyl)-20S-amino-pregn-5-en-3β-yl 6-(2-tetrahydropyranyloxy)hexyl ether Step B: N-(2,2,2-Trichloro-ethoxycarbonyl)-20S-amino-pregn-5-en-3β-yl 6-hydroxyhexyl ether Step C: N-(2,2,2-Trichloro-ethoxycarbonyl)-20S-amino-pregn-5-en-3β-yl 6-iodohexyl ether Step D: 6-(N-(2,2,2-Trichloro-ethoxycarbonyl)-20S-amino-pregn-5-en-3β-yloxy)hexyl 1-thio-β-D-mannopyranoside Step E: 6-(20S-amino-pregn-5-en-3β-yloxy)hexyl 1-thio-β-D-mannopyranoside

EXAMPLE 15

In vivo Stimulation of Host Resistance *Pseudomonas aeruginosa* in vivo Protection Studies.

Groups of 15-20 CF1 female mice (Charles River Breeding, Cambridge, Mass.) weighing 22-28 gm were injected intraperitoneally (i.p.) with cyclophosphamide (Cytoxan; CY) at 250 mg per kg body weight. One to two hours later they were typically injected again with the test material by the route specified. Four days later, the mice were divided into groups of five, each of which were injected i.p. with a different dilution of a suspension of *Pseudomonas aeruginosa* (Immunotype 1). The number of survivors was determined periodically and an estimate was made of the number of CFU of Pseudomonas organisms necessary to cause 50% lethality by the cumulative method of L. J. Reed and H. Muench (*Am. J. Hygiene* 27 (1938) 493–497). A protective index (P.I.) was defined as the $LD_{50}$ for the mice receiving cyclophosphamide and the test compound divided by the $LD_{50}$ for the mice receiving cyclophosphamide alone. All control mice were injected with aqueous vehicle in the same route and schedule as the test animals.

MATERIALS. All compounds for dosing were suspended in a sterile medium referred to as "aqueous vehicle" which contains 0.9% sodium chloride, 0.5% carboxymethyl cellulose, 0.4% Tween 80, and 0.9% benzyl alcohol unless otherwise stated. Test materials were evaluated via subcutaneous (s.c.), i.p., intramuscular (i.m.), orally (p.o.) and intravenous (i.v.) routes of administration. The initial test dose was 40 mg per kg per mouse, with each active compound subsequently titrated below this level.

INFECTION OF ANIMALS. All bacteria were inoculated i.p. to induce infection in the in vivo experiments. *Candida albicans*, however, was administrated i.v. Bacteria cultures were harvested in the log phase, washed with phosphate buffered saline (PBS, and resuspended in PBS containing 10% glycerol for freezing at −70° C. in 1 ml aliquots. The number of cell free units (cfu's) was determined before and after freezing. Frozen cultures were routinely thawed and diluted in sterile PBS just prior to inoculation. Viable cell counts were routinely done on thawed cultures the day of challenge to determine the number of cfu's. *Candida albicans* was stored in distilled water at room temperature. Viable cell counts were determined the day of testing.

The testing and results of 6-(5-cholesten-3β-yloxy)-hexyl-1-thio-β-D-mannopyranoside (Example 2) against various organisms is shown in Table 2. The results of other claimed compounds tested for protection against *Pseudomonas aeruginosa* infection are shown in Table 3.

TABLE 2

Protection from Infection by Various Organisms by 6-(5-Cholesten-3β-yloxy)hexyl-1-thio-β-D mannopyranoside.

| Treatment | | | $LD_{50}$ | |
|---|---|---|---|---|
| CY | Dose mg/kg | Organism | Actual | P.I. (log) |
| − | − | PA | $1.89 \times 10^7$ | 5.52 |
| Control + | − | PA | $5.67 \times 10^1$ | D |
| + | 10 | PA | $3.2 \times 10^4$ | 2.75 |
| + | 20 | PA | $3.2 \times 10^5$ | 3.75 |
| + | 40 | PA | $1.22 \times 10^6$ | 4.33 |
| + | 80 | PA | $2.59 \times 10^6$ | 4.66 |
| − | − | SA | $3.38 \times 10^6$ | 1.99 |
| Control + | − | SA | $3.45 \times 10^4$ | 0 |
| + | 5 | SA | $3.38 \times 10^5$ | 0.99 |
| + | 10 | SA | $1.04 \times 10^6$ | 1.47 |
| + | 20 | SA | $2.38 \times 10^6$ | 1.83 |
| + | 40 | SA | $1.58 \times 10^7$ | 2.66 |
| − | − | CA | $7.88 \times 10^4$ | 1 |
| Control + | − | CA | $7.88 \times 10^3$ | 0 |
| + | 10 | CA | $3.68 \times 10^4$ | 0.67 |
| + | 20 | CA | $5.2 \times 10^4$ | 0.81 |
| + | 40 | CA | $7.88 \times 10^4$ | 1 |
| − | − | KP | $1 \times 10^8$ | 1.45 |
| Control + | − | KP | $3.53 \times 10^6$ | 0 |
| + | 40 | KP | $4.73 \times 10^7$ | 1.12 |

Key to table 2.
CY = Cytoxan
SC = Sub cutaneous administration
PA = *Pseudomonas aeruginosa* (Gram Negative bacteria)
SA = *Staphylococcus aureus* (Gram Positive bacteria)
CA = *Candida albicans* (fungus)
KP = *Klebsiella pheumoniae* (Gram Negative bacteria)

$$PI = \frac{LD_{50} \text{ Test}}{LD_{50} \text{ CY Control}}$$

TABLE 3

Stimulation of Host Resistance Against *Pseudomonas Aeruginosa*

| Compound (Same numbering as Example) | Protective Index (log) |
|---|---|
| 1. 6-(5-Cholesten-3β-yloxy)hexyl 1-thio-α-D-mannopyranoside | 1.5 |
| 2. 6-(5-Cholesten-3β-yloxy)hexyl 1-thio-β-D-mannopyranoside | 4.5 |
| 3. 6-(5-Cholesten-3β-yloxy)hexyl 1-thio-α-L-fucopyranoside | 2.8 |
| 4. 6-(5-Cholesten-3β-yloxy)hexyl 1-thio-β-L-fucopyranoside | 1.3 |
| 5. 2-(2-(5-Cholesten-3β-yloxy)ethoxy)-ethyl 1-thio-α-D-mannopyranoside | 1.7 |
| 6. 6-(Stigmasta-5,22-dien-3β-yloxy)hexyl 1-thio-β-D-mannopyranoside | 2.0 |
| 7. 6-(Pregn-5-en-20-one-3β-yloxy)hexyl 1-thio-β-D-mannopyranoside | 3.5 |
| 8. 6-(17β-Carbomethoxy-androst-5-en-3β-yloxy)hexyl 1-thio-β-D-mannopyranoside | 2.5 |
| 9. 6-(17β-Carbamido-androst-5-en-3β-yloxy)-hexyl 1-thio-β-D-mannopyranoside | 2.5 |
| 10. 6-(Pregn-5-en-20-ol-3β-yloxy)hexyl 1-thio-β-D-mannopyranoside | 1.3 |
| 11. 6-(20S-Acetamido-pregn-5-en-3β-yloxy)-hexyl 1-thio-β-D-mannopyranoside | 3.0 |
| 12. 6-(20R-Acetamido-pregn-5-en-3β-yloxy)-hexyl 1-thio-β-D-mannopyranoside | 2.6 |
| 13. 6-(20S-Amino-pregn-5-en-3β-yloxy)hexyl 1-thio-β-D-mannopyranoside | 4.37 |
| 14. 6-(20R-Amino-pregn-5-en-3β-yloxy)hexyl 1-thio-β-D-mannopyranoside | 4.37 |

As is seen from the data, these compounds are very potent immunostimulators, protecting an immunocompromised host from death resulting from opportunistic infection.

EXAMPLE 16

An antiviral experiment was conducted to compare treatment with 6-(5-Cholesten-3β-yloxy)hexyl 1-thio-β-D-mannopyranoside (Example 2) in mice infected IP with Herpes Simplex Virus-1 (HSV1) immediately before (post treatment) or after 5 days of treatment (pretreatment).

Ten mice (ICR, 20 gm, mixed sexes) were pretreated by SC injection of a 0.1 mL suspension of test compound twice a day for 4 days. On day 5, the mice were injected IP with 0.5 mL solution of HSV1 (Schloser, 10-5). The post treatment group was infected with HSV1 prior to administration of test compound. Day of death from time of infection with HSV1 was recorded for each mouse and average day of death per treatment group was calculated. One-way analysis of variance was performed and the statistically significant results are presented in Table 4.

TABLE 4

| Dose (mg/kg) | Average Day of Death | | P |
|---|---|---|---|
| | Post Treatment | Pre Treatment | |
| 50 | 6.4 | 11.0* | 0.003 |
| 12.5 | 7.5 | 8.0 | 0.725 |
| 3.1 | 6.3 | 7.1 | 0.348 |
| 0.8 | 9.1 | 8.6 | 0.797 |
| Placebo | 7.5 | 7.5 | 0.992 |

*Statistically different from placebo.

This data indicates that a dose of 50 mg/kg twice a day for four days of the test compound offers statistically enhanced protection from fatal viral infection over placebo treated animals as measured by day of death. Also, mice pretreated with test compound showed statistically enhanced protection over the post treatment group.

It is reasonably believed on the basis of the data that the disclosed invention pharmaceutical compounds herein will provide a human host with enhanced resistance to viral infection; and further provide a human host, who is immunocompromised as a result of infection or contact with an AIDS-related virus, with enhanced host resistance to opportunistic bacterial, fungal, viral or cancerous infection, including Kaposi's sarcoma and Pneumocystis pneumonia.

What is claimed is:

1. A method for enhancing human host resistance against opportunistic infection in an individual immunocompromised by an Auto-immune Deficiency Syndrome (AIDS)-related virus consisting essentially of the step of administering to said individual a therapeutically effective amount of a pharmaceutical composition consisting of an anti-viral, anti-AIDS drug selected from the group consisting of azidothymidine, AL721, ansamycin, foscarnet, HPA-23, ribavirin and dideoxycytidine and a qlycolipid compound consisting essentially of the formula:

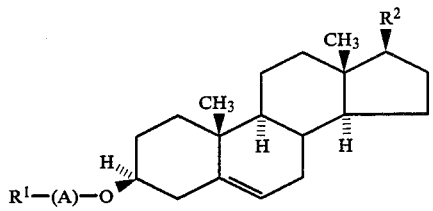

where:
$R^1$ is α or β-D-1-thiomannopyranoside, α or β-L-1-thiofucopyranoside;

A is $(CH_2)_n$ where n is 5–7, or $(CH_2)_k X(CH_2)_m$ where X is O S or NH and k and m are independently 2–4 and the sum of k and m is 4–6;

$R^2$ is $C_1$–$C_8$ linear or branched alkyl or $C_2$–$C_{10}$ linear or branched alkene;

where
where B is $C_1$–$C_8$ alkyl, $C_1$–$C_8$ alkoxy, $NR^3R^4$ where $R^3$ and $R^4$ are independently H, $C_1$–$C_4$ alkyl; $CH(CH_3)D$ where D is OH, $NH_2$, $NHR^5$ where $R^5$ is $C_1$–$C_{10}$ alkyl;

or pharmaceutically acceptable salts thereof, said composition also containing a pharmaceutically acceptable carrier therefor, wherein said anti-viral, anti-AIDS drug is present in a weight ratio from about 1:3 to about 3:1 based on the weight of said glycolipid compound.

2. The method of claim 1 wherein said glycolipid compound is present in an amount effective to exert an immunostimulant effect.

3. The method of claim 1 wherein $R^2$ is a cholesterol 17-side chain.

4. The method of claim 1 wherein $R^2$ is a stigmasterol 17-side chain.

5. The method of claim 1 wherein

6. The method of claim 1 wherein CH(CH₃)D is CH₃—CHOH—, CH₃CH(NHCOCH₃)—, or CH₃CH(NH₂)—.

7. The method of claim 1 wherein said glycolipid compound is selected from the group consisting of:
6-(5-Cholesten-3β-yloxy)hexyl-1-thio-α-D-mannopyranoside;
6-(5-Cholesten-3β-yloxy)hexyl-1-thio-β-D-mannopyranoside;
6-(5-Cholesten-3β-yloxy)hexyl-1-thio-α-L-fucopyranoside;
6-(5-Cholesten-3β-yloxy)hexyl-1-thio-β-L-fucopyranoside; 2-(2-(5-Cholesten-3β-yloxy)ethoxy)ethyl-1-thio-β-D-mannopyranoside;
6-(Stigmasta-5,22-dien-3β-yloxy)hexyl-1-thio-β-D-mannopyranoside;
6(Pregn-5-en-20-one-3β-yloxy)hexyl-1-thio-β-D-mannopyranoside;
6-(17β-Carbomethoxy-androst-5-en-3β-yloxy)hexyl-1-thio-β-D-mannopyranoside;
6-(17β-Carbamido-androst-5-en-3β-yloxy)-hexyl-1-thio-β-D-mannopyranoside;
6-(Pregn-5-en-20-ol-3β-yloxy)hexyl-1-thio-β-D-mannopyranoside;
6-(20S-Acetamido-pregn-5-en-3β-yloxy)-hexyl-1-thio-β-D-mannopyranoside;
6-(20R-Acetamido-pregn-5-en-3β-yloxy)-hexyl-1-thio-β-D-mannopyranoside;
6-(20S-Amino-pregn-5-en-3β-yloxy)hexyl-1-thio-β-D-mannopyranoside; or
6-(20R-Amino-pregn-5-en-3β-yloxy)hexyl-1-thio-β-D-mannopyranoside.

8. The method of claim 1 wherein glycolipid compound is 6-(5-chloesten-3β-yloxy)hexyl-1-thio-β-D-mannopyranoside.

9. The composition of claim 1 wherein said composition is administered intramuscularly, subcutaneously or intraperitoneally.

10. The method of claim 1 wherein said glycolipid compound is present in a noncrystalline form.

* * * * *